May 12, 1964 E. S. BOERNER Plant Pat. 2,400
ROSE PLANT
Filed June 4, 1963
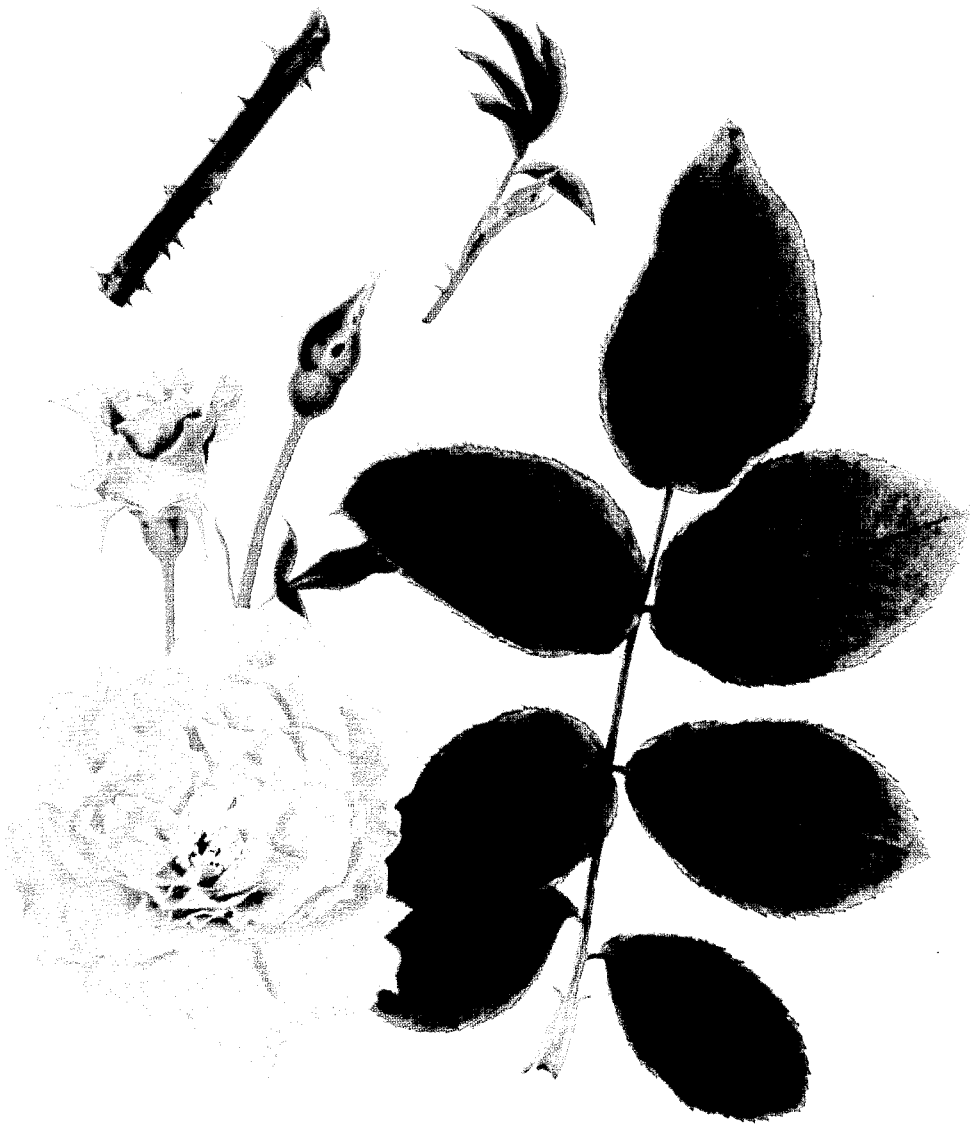
Inventor.
E. S. Boerner
By: Robb & Robb
Attorneys.

United States Patent Office

Plant Pat. 2,400
Patented May 12, 1964

2,400
ROSE PLANT

Eugene S. Boerner, Newark, N.Y., assignor to Jackson & Perkins Company, Newark, N.Y., a corporation of New York Filed June 4, 1963, Ser. No. 285,536
1 Claim. (Cl. Plt.—20)

The present invention relates to a new and distinct variety of rose plant of the hybrid tea class, which was originated by me by crossing the variety "Spartan" (Plant Patent No. 1,357) with the variety "Golden Masterpiece" (Plant Patent No. 1,284).

The primary object of this breeding was to improve the plant habit of the parent variety "Golden Masterpiece," This objective was fully achieved, along with other desirable improvements, as evidenced by the following unique combination of characteristics which are outstanding in the new variety and which distinguish it from its parents, as well as from all other varieties of which I am aware:

(1) A strong and bushy habit of plant growth;

(2) Excellent Empire Green foliage borne on Carmine leaf stems, with Carmine veins in the leaflets;

(3) A very free blooming habit throughout the growing season;

(4) Well-shaped buds and flowers, said buds being ovoid and having flaring outer petals as the buds open, which is a distinct characteristic of this new variety; and (5) A distinctive and attractive general color tonality of the flowers corresponding to Scarlet-Red, very lightly overcast with Scarlet.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in color illustration of this character.

The following is a detailed description of my new variety, with color terminology in accordance with Ridgway's Color Standards and Nomenclature:

Parentage: Seedling.
*Seed parent.*—"Spartan."
*Pollen parent.*—"Golden Masterpiece."
Classification:
*Botanic.*—Hybrid tea.
*Commercial.*—Hybrid tea.

*Flower*

(Observations made from specimens grown outdoors at Newark, New York, near mid-morning during the middle of the month of September.)

Blooming habit: Recurrent—continuous.
Bud:
*Size.*—Large.
*Form.*—Ovoid; with flaring outer petals; is not affected by wet or hot weather.
*Color.*—When sepals first divide—Scarlet-Red, Plate 1. When petals begin to unfurl—Spectrum Red, Plate 1, lightly overcast with Scarlet, Plate 1. When half-blown: inside of petals—Scarlet, Plate 1; reverse of petals—Scarlet-Red, Plate 1, lightly overcast with Scarlet, Plate 1.
*Sepals.*—Slightly branched; curl back when petals begin to unfurl. Color: inside—Pale Tiber Green, Plate 18; outside—Light Bice Green, Plate 17, lightly overcast with Pompeian Red, Plate 13.

*Calyx.* — Color — Light Bice Green, Plate 17. Shape—apple. Size—small. Aspect—smooth. Odor when rubbed—none.
*Peduncle.* — Length — medium. Aspect — rough. Strength—erect; slender. Color—Biscay Green, Plate 17.
*Opening.*—Opens up well; is not affected by adverse weather conditions.
Bloom:
*Size.*—Large. Average size when fully expanded—5 inches.
*Borne.*—Both singly and several together; produces very freely.
*Stems.*—Long; strong.
*Form (when first open.)*—Cupped and high-centered. Permanence—retains its form to the end.
*Petalage.*—Double (full but open center). Number of petals under normal conditions—from 50 to 55.
*Color.*—Center of flower—Scarlet-Red, Plate. Outer petals—Scarlet, Plate 1. Base of petals (aiglet)—Lemon Yellow, Plate 4. Inside of petals—Scarlet-Red, Plate 1, very lightly overcast with Scarlet, Plate 1. Reverse of petals—Scarlet, Plate 1, very lightly overcast with Spectrum Red, Plate 1. General tonality from a distance—Scarlet-Red, Plate 1, lightly overcast with Scarlet, Plate 1.
*Discoloration.*—General tonality at end of first day—Scarlet-Red, Plate 1. Second day—Scarlet-Red, Plate 1, lightly overcast with Scarlet, Plate 1. Third day—Scarlet, Plate 1.
Petals:
*Texture.*—Leathery; is not affected by wet or hot weather.
*Appearance.*—Inside—satiny. Outside—shiny.
*Form.*—Oval.
*Arrangement.*—Imbricated (regularly arranged shingle-like).
*Petaloids in center.*—Few; large.
*Persistence.*—Drop off cleanly.
*Fragrance.*—Moderate. Nature—tea (average hybrid tea scent).
*Lasting quality.*—On the plant—long. As cut flower—long.

*Genital Organs*

Stamens, Anthers: Medium size; many; regularly arranged around styles. Color—Pinard Yellow, Plate 4.
Stamens, Filaments (threads): Medium length. Color—Martius Yellow, Plate 4.
Pollen: Color—Baryta Yellow, Plate 4.
Styles: Bunched; uneven length; short; thin.
Stigmas: Color—Sulphur Yellow, Plate 5.
Ovaries: All enclosed in calyx.
Hips: None.
Seeds: None.

*Plant*

Form: Bush.
Growth: Vigorous; upright; bushy.
Foliage: Compound of 3–7 leaflets.
*Size.*—Large.
*Quantity.*—Abundant.
*Color.*—New foliage: upper side—Pompeian Red, Plate 13; under side—Brick Red, Plate 13. Old foliage: upper side—Empire Green, Plate 32; under side—Jade Green, Plate 31.
*Shape.*—Oval.
*Texture.* — Upper side — leathery. Under side—smooth.
*Ribs and veins.*—Ordinary. Color (of veins)—Carmine, Plate 1.
*Edge.*—Serrated (saw-toothed).
*Serration.*—Both double and single; small.

*Leaf stem.*—Color—Carmine, Plate 1. Under side—smooth.

*Stipules.*—Medium length; bearded.

Wood:

*New wood.*—Color—Biscay Green, Plate 17. Bark—smooth.

*Old wood.*—Color—Light Hellebore Green, Plate 17. Bark—smooth.

Thorns:

*Thorns.*—Quantity: on main stalks from base—many; on laterals from stalk—many. Form—narrow base; medium length; hooked downward. Color (when young)—Eugenia Red, Plate 13. Position—Irregular.

*Prickles.*—Quantity: on main stalks—none; on laterals—none.

*Short needles.*—Quantity: on main stalks—none; on laterals—none.

I claim:

A new and distinct variety of rost plant of the hybrid tea class, substantially as herein shown and described, characterized particularly as to novelty by the unique combination of a strong and bushy habit of growth, excellent Empire Green foilage borne on Carmine leaf stems and having Carmine veins in the leaflets, a very free blooming habit throughout the growing season, well-shaped buds and flowers, said buds being of ovoid form with flaring outer petals, and a distinctive and attractive general color tonality of the flowers corresponding to Scarlet-Red, very lightly overcast with Scarlet.

No references cited.